(12) United States Patent  (10) Patent No.: US 7,951,953 B2
Fagan  (45) Date of Patent: May 31, 2011

(54) CONVERSION OF 2-PYRAZOLINES TO PYRAZOLES USING BROMINE

(75) Inventor: Paul Joseph Fagan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 804 days.

(21) Appl. No.: 11/885,325

(22) PCT Filed: Mar. 14, 2006

(86) PCT No.: PCT/US2006/009617
§ 371 (c)(1),
(2), (4) Date: Aug. 30, 2007

(87) PCT Pub. No.: WO2006/102025
PCT Pub. Date: Sep. 28, 2006

(65) Prior Publication Data
US 2008/0177078 A1  Jul. 24, 2008

(51) Int. Cl.
*C07D 401/04* (2006.01)
*C07D 231/16* (2006.01)
*C07D 231/22* (2006.01)

(52) U.S. Cl. ............... 546/275.4; 546/276.1; 548/369.7; 548/374.1

(58) Field of Classification Search ............... 546/275.4, 546/276.1; 548/369.7, 374.1
See application file for complete search history.

(56) References Cited

FOREIGN PATENT DOCUMENTS
WO  03/016283 A1  2/2003

OTHER PUBLICATIONS

Dorwald, Side Reactions in Organic Synthesis, 2005, Wiley: VCH Weinheim Preface, pp. 1-15 & Chapter 8, pp. 279-308.*
V. Auwers, Spectrochemisty of Pyrazolines, Justus Liebigs Ann. Chem., 1927, vol. 458:175-186.
Iturrino et al., Synthesis, Cytostatic and Trichomonacide Activities of 3,5-BIS -(halomethyl) Pyrazoles, Eur. J. Med. Chem., 1987, vol. 22:445-451.
G. H. Sayed, Synthesis, of Some New Pyrazolines From 4-Nitro- & 4-Chloro-4-Methoxybenzalacetophenones, Indian Journal of Chemistry, 1980, vol. 19B:364-367.
Mokhtar et al., Triazol-Pyrazole Compounds With Possible Biological Activity, Pak. J. Sci. Ind. Res., 1992, vol. 35:428-433.
Auwers, on Pyrazolines, Justus Liebigs Ann. Chem., 1932, vol. 496:186-220.
Curzu et al., A Facile Synthesis of 3-Aryl-4-Pyrazoleactic Acids and of Their 4,5-Dihydro Derivatives, Heterocycl. Chem., 1990, vol. 27:205-208.
Faid-Allah et al., Pyrazole Derivatives With Possible Hypoglycemic Activity, Indian Journal of Chemistry, 1988, vol. 27B:245-249.
Sato et al., Synthesis of 3-Barbamoyl-4-[B-D-ribofuranosyl)methyl]pyrazole, A Pyrazole Homo-C Nucleoside, The Chemical Society of Japan, 1980, vol. 53:1195-1196.

(Continued)

*Primary Examiner* — Patricia L Morris

(57) ABSTRACT

This invention relates to a method for preparing a compound of Formula 1 wherein L, $R^1$, $R^2$ and X are as defined in the disclosure, comprising contacting a 2 pyrazoline of Formula 2 with bromine at a temperature of at least about 80° C. (Formula 1) (Formula 2). This invention also discloses preparation of a compound of Formula 3 wherein X, Z, $R^5$, $R^6$, $R^7$, $R^{8a}$, $R^{8b}$ and n are as defined in the disclosure, using a compound of Formula 1a wherein $R^{10}$ is as defined in the disclosure, prepared by the aforesaid method for preparing a compound of Formula 1. (Formula 3) (Formula 4).

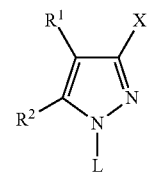

1

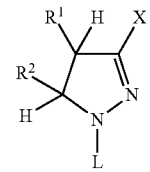

2

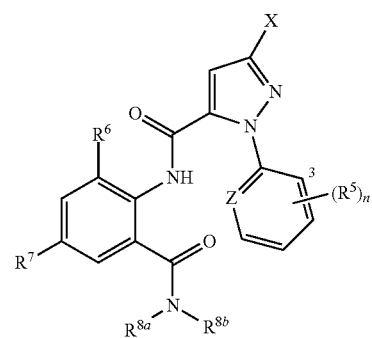

3

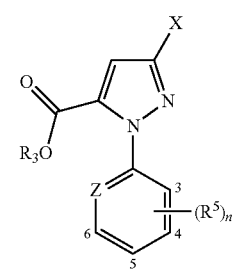

1a

13 Claims, No Drawings

OTHER PUBLICATIONS

Soliman et al., Preparation and Antidiabetic Activity of New Substituted 3,5-Diarylpyrazolesulfonylurea Derivatives II: Structure-Activity Relationship, J. Pharm. Sci., 1987, vol. 76:626-632.

Faidallah et al., Synthesis and Reactions of Some Ethyl 3-Aroyl-4-Aryl-2-Pyrazoline-5-Carboxylates, Pharmazie, 1997, vol. 52:101-105.

Faidallah et al., Synthesis and Reactions of Some Ethyl 3(5)Aroyl-4-Aryl-2-Pyrazoline-3 (3) Carboxylates, Rev. Roum. Chim., 1997, vol. 42:1141-1153.

Faidallah et al., Pakistan Journal of Scientific and Industrial Research, Pak. J. Sci. Ind. Res., 1995, vol. 38: 179-181.

El-Sadek et al., Synthesis and Spectral Studies of Some New Pyrazolines and Pyrazoles, Egypt J. Chem., 1995, vol. 38:403-418.

A. P. Molchanov et. al., Reactions of Aliphatic Diazo Compounds: III. Reaction of Ethyl Diazoacetate with 1,3-Diarylpropenone, Russian Journal of Organic Chemistry, 2001, vol. 37:1517-1521.

R.H. Wiley, Pyrazoles, Pyrazolines, Pyrazolidies, Indazoles and Condensed Rings, Interscience, 1967, pp. 215-217, XP002387813.

Kevin T. Potts et al., The Synthesis of 3H-1,2,4-Thiadiazolo[3,4-b]Benzothiazoles, J. Heterocyclic Chem., 26, 1289 (1989).

* cited by examiner

CONVERSION OF 2-PYRAZOLINES TO PYRAZOLES USING BROMINE

FIELD OF THE INVENTION

This invention relates to converting 4,5-dihydro-1H-pyrazoles (also known as 2-pyrazolines) to corresponding pyrazoles.

BACKGROUND OF THE INVENTION

PCT Patent Publication WO 03/016283 discloses a process of preparing pyrazoles of Formula i

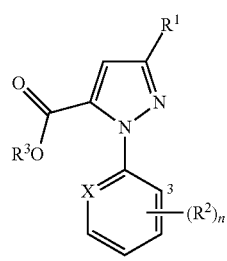

i wherein $R^1$ is halogen; $R^2$ is, inter alia, $C_1$-$C_4$ alkyl, $C_1$-$C_4$ haloalkyl, halogen, CN, $C_1$-$C_4$ alkoxy or $C_1$-$C_4$ haloalkoxy; $R^3$ is $C_1$-$C_4$ alkyl; X is N or $CR^4$; $R^4$ is H or $R^2$; and n is 0 to 3, provided when X is CH then n is at least 1 which are useful as intermediates to insecticides. The method involves treatment of the corresponding 2-pyrazoles of Formula ii with an oxidizing agent optionally in the presence of acid.

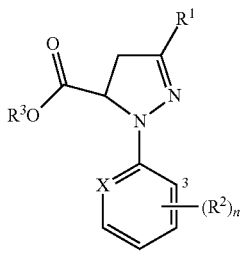

ii

When X is $CR^2$, the preferred oxidant is hydrogen peroxide; and when X is N, the preferred oxidant is potassium persulfate. However, the need continues for new methods that are less costly, more efficient, more flexible, or more convenient to operate.

SUMMARY OF THE INVENTION

This invention is directed to a method for preparing a compound of Formula 1,

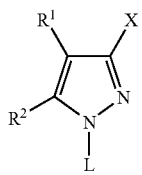

1 wherein
X is H, halogen, $OR^3$ or an optionally substituted carbon moiety;

L is an optionally substituted carbon moiety;
$R^1$ is H or an optionally substituted carbon moiety;
$R^2$ is H, an optionally substituted carbon moiety, $NO_2$ or $SO_2R^4$;
$R^3$ is H or an optionally substituted carbon moiety; and
$R^4$ is an optionally substituted carbon moiety;
the method comprising contacting a 2-pyrazoline of Formula 2

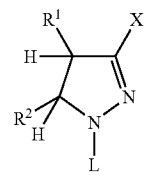

2 with bromine at a temperature of at least about 80° C.

This invention also relates to a method of preparing a compound of Formula 3

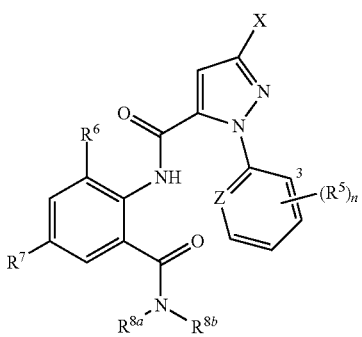

3 wherein
Z is N or $CR^9$;
each $R^5$ is independently halogen or $C_1$-$C_4$ haloalkyl;
$R^6$ is $CH_3$, F, Cl or Br; and
$R^7$ is F, Cl, Br, I, CN or $CF_3$;
$R^{8a}$ is $C_1$-$C_4$ alkyl;
$R^{8b}$ is H or $CH_3$;
$R^9$ is H, halogen or $C_1$-$C_4$ haloalkyl; and
n is an integer from 0 to 3
using a compound of Formula 1a

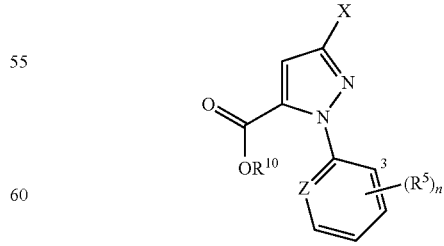

1a wherein $R^{10}$ is H or an optionally substituted carbon moiety; the method characterized by preparing the compound of Formula 1a (i.e. a subgenus of Formula 1) by the method as disclosed above.

DETAILED DESCRIPTION OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

In the recitations herein, the term "carbon moiety" refers to a radical in which a carbon atom is connected to the remainder of Formulae 1 and 2. As the carbon moieties L, $R^1$, $R^2$, $R^3$, $R^4$, $R^{10}$ and X are substituents separated from the reaction center, they can encompass a great variety of carbon-based groups preparable by modern methods of synthetic organic chemistry. The method of this invention is generally applicable to a wide range of starting compounds of Formula 2 and product compounds of Formula 1. It is generally preferred that the carbon moieties are not sensitive to bromine under reaction condition. However, this present invention is particular suitable for converting compounds of Formula 2 having carbon moieties that are sensitive to bromine under other reaction conditions (e.g., temperature below 80° C.). "Carbon moiety" thus includes alkyl, alkenyl and alkynyl, which can be straight-chain or branched. "Carbon moiety" also includes carbocyclic and heterocyclic rings, which can be saturated, partially saturated, or completely unsaturated. Furthermore, unsaturated rings can be aromatic if Hückel's rule is satisfied. The carbocyclic and heterocyclic rings of a carbon moiety can form polycyclic ring systems comprising multiple rings connected together. The term "carbocyclic ring" denotes a ring wherein the atoms forming the ring backbone are selected only from carbon. The term "heterocyclic ring" denotes a ring wherein at least one of the ring backbone atoms is other than carbon. "Saturated carbocyclic" refers to a ring having a backbone consisting of carbon atoms linked to one another by single bonds; unless otherwise specified, the remaining carbon valences are occupied by hydrogen atoms. The term "aromatic ring system" denotes fully unsaturated carbocycles and heterocycles in which at least one ring in a polycyclic ring system is aromatic. Aromatic indicates that each of ring atoms is essentially in the same plane and has a p-orbital perpendicular to the ring plane, and in which (4n+2) π electrons, when n is 0 or a positive integer, are associated with the ring to comply with Hückel's rule. The term "aromatic carbocyclic ring system" includes fully aromatic carbocycles and carbocycles in which at least one ring of a polycyclic ring system is aromatic. The term "nonaromatic carbocyclic ring system" denotes fully saturated carbocycles as well as partially or fully unsaturated carbocycles wherein none of the rings in the ring system are aromatic. The terms "aromatic heterocyclic ring system" and "heteroaromatic ring" include fully aromatic heterocycles and heterocycles in which at least one ring of a polycyclic ring system is aromatic. The term "nonaromatic heterocyclic ring system" denotes fully saturated heterocycles as well as partially or fully unsaturated heterocycles wherein none of the rings in the ring system are aromatic. The term "aryl" denotes a carbocyclic or heterocyclic ring or ring system in which at least one ring is aromatic, and the aromatic ring provides the connection to the remainder of the molecule.

The carbon moieties specified for L, $R^1$, $R^2$, $R^3$, $R^4$, $R^{10}$ and X are optionally substituted. The term "optionally substituted" in connection with these carbon moieties refers to carbon moieties that are unsubstituted or have at least one non-hydrogen substituent. Illustrative optional substituents include alkyl, alkenyl, cycloalkyl, cycloalkenyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, cycloalkoxy, aryloxy, alkylthio, alkenylthio, alkynylthio, cycloalkylthio, arylthio, alkylsulfinyl, alkenylsulfinyl, alkynylsulfinyl, cycloalkylsulfinyl, arylsulfinyl, alkylsulfonyl, alkenylsulfonyl, alkynylsulfonyl, cycloalkylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyl, alkenylaminocarbonyl, alkynylaminocarbonyl, arylaminocarbonyloxy, alkoxycarbonylamino, alkenyloxycarbonylamino, alkynyloxycarbonylamino and aryloxycarbonylamino, each further optionally substituted; and halogen, cyano and nitro. The optional further substituents are independently selected from groups like those illustrated above for the substituents themselves to give additional substituent groups for L, $R^1$, $R^2$, $R^3$, $R^4$, $R^{10}$ and X such as haloalkyl, haloalkenyl and haloalkoxy. As a further example, alkylamino can be further substituted with alkyl, giving dialkylamino. The substituents can also be tied together by figuratively removing one or two hydrogen atoms from each of two substituents or a substituent and the supporting molecular structure and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—CH$_2$—O—. Tying together a hydroxy group and the molecular structure to which it is attached can give cyclic ethers, including epoxides. Illustrative substituents also include oxygen, which when attached to carbon forms a carbonyl function. Similarly, sulfur when attached to carbon forms a thiocarbonyl function. As the 4,5-dihydropyrazole moiety of Formula 2 constitutes one ring, tying together $R^1$ and $R^2$ or L and $R^2$, would result in a fused bicyclic or polycyclic ring system.

As referred to herein, "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers: "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "alkenylthio", "alkenylsulfinyl", "alkenylsulfonyl", "alkynylthio", "alkynylsulfinyl", "alkynylsulfonyl", and the like, are defined analogously to the above examples. Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2C(=O)$, $CH_3CH_2CH_2OC(=O)$, $(CH_3)_2CHOC(=O)$ and the different butoxy- or pentoxycarbonyl isomers. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)(cycloalkyl)amino" means a cycloalkylamino group where the amino hydrogen atom is replaced by an alkyl radical; examples include groups such as (methyl)(cyclopropyl)amino, (butyl)(cyclobutyl)amino, (propyl)cyclopentylamino, (methyl)cyclohexylamino and the like. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$.

The total number of carbon atoms in a substituent group is indicated by the "$C_i$-$C_j$" prefix where i and j are, for example, numbers from 1 to 3; e.g., $C_1$-$C_3$ alkyl designates methyl through propyl.

As indicated above, the carbon moieties L, $R^1$, $R^2$, $R^3$, $R^4$, $R^{10}$ and X may comprise an aromatic ring or ring system. Examples of aromatic rings or ring systems include a phenyl ring, 5- or 6-membered heteroaromatic rings aromatic 8-, 9- or 10-membered fused carbobicyclic ring systems and aromatic 8-, 9- or 10-membered fused heterobicyclic ring systems wherein each ring or ring system is optionally substituted. The term "optionally substituted" in connection with these L, $R^1$, $R^2$, $R^3$, $R^4$, $R^{10}$ and X carbon moieties refers to carbon moieties which are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. An example of phenyl optionally substituted with from one to four substituents is the ring illustrated as U-1 in Exhibit 1, wherein $R^v$ is any non-hydrogen substituent and r is an integer from 0 to 4. Examples of aromatic 8-, 9- or 10-membered fused carbobicyclic ring systems optionally substituted with from one to four substituents include a naphthyl group optionally substituted with from one to four substituents illustrated as U-85 and a 1,2,3,4-tetrahydronaphthyl group optionally substituted with from one to four substituents illustrated as U-86 in Exhibit 1, wherein $R^v$ is any substituent and r is an integer from 0 to 4. Examples of 5- or 6-membered heteroaromatic rings optionally substituted with from one to four substituents include the rings U-2 through U-53 illustrated in Exhibit 1 wherein $R^v$ is any substituent and r is an integer from 1 to 4. Examples of aromatic 8-, 9- or 10-membered fused heterobicyclic ring systems optionally substituted with from one to four substituents include U-54 through U-84 illustrated in Exhibit 1 wherein $R^v$ is any substituent and r is an integer from 0 to 4. Other examples of L and R include a benzyl group optionally substituted with from one to four substituents illustrated as U-87 and a benzoyl group optionally substituted with from one to four substituents illustrated as U-88 in Exhibit 1, wherein $R^v$ is any substituent and r is an integer from 0 to 4.

Although $R^v$ groups are shown in the structures U-1 through U-85, it is noted that they do not need to be present since they are optional substituents. The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formulae 1 and 2 through any available carbon of the U group by replacement of a hydrogen atom.

Exhibit 1

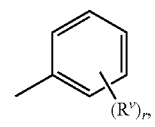
U-1

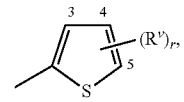
U-2

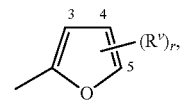
U-3

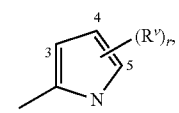
U-4

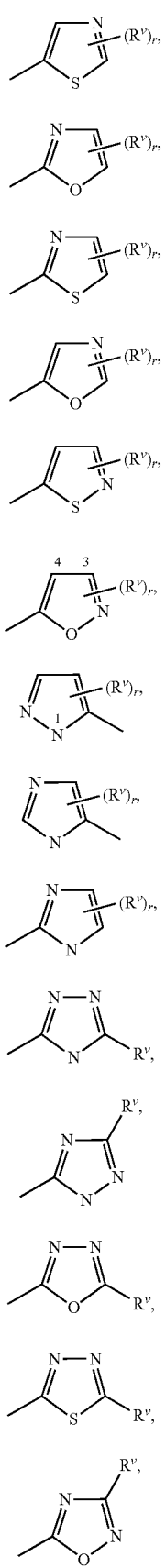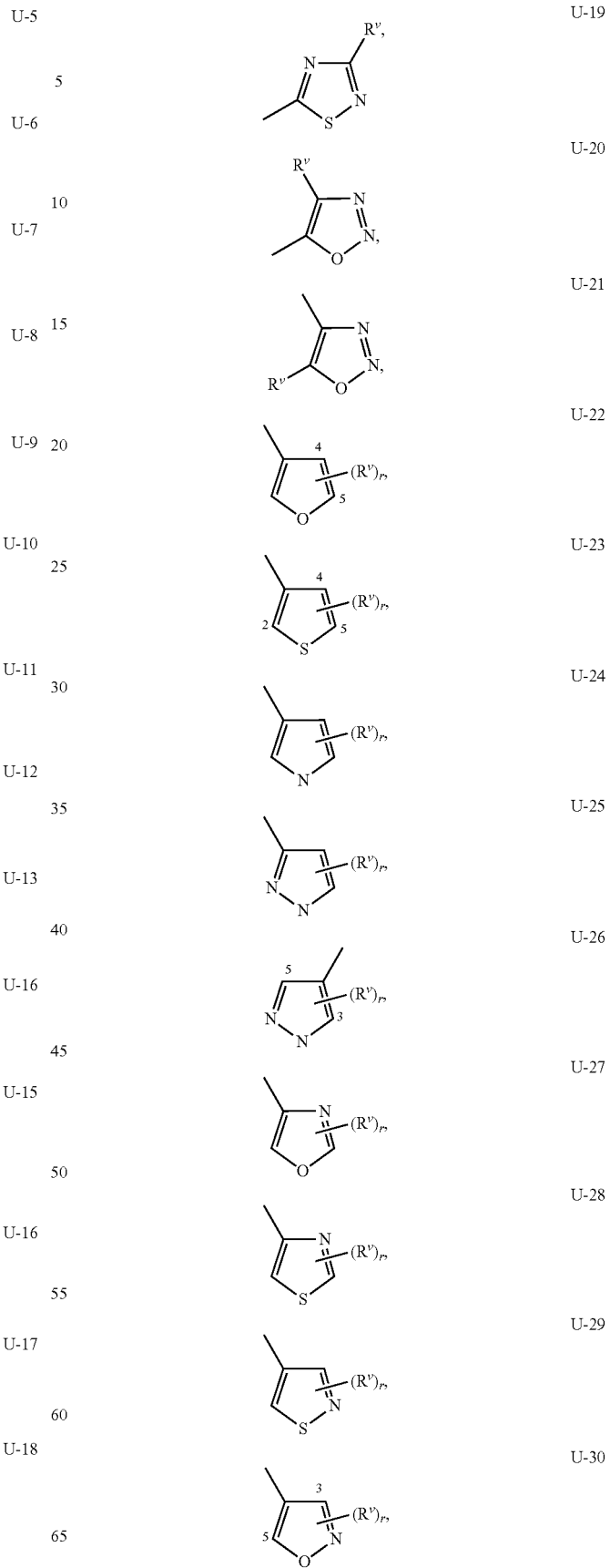

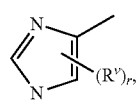 U-31
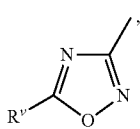 U-32
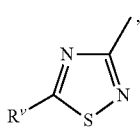 U-33
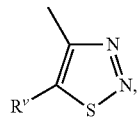 U-34
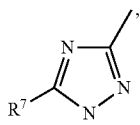 U-35
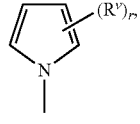 U-36
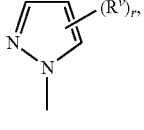 U-37
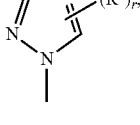 U-38
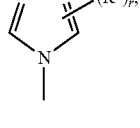 U-39
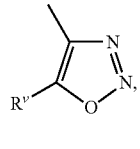 U-40
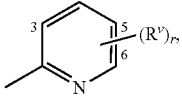 U-41
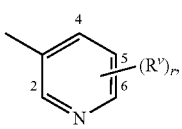 U-42
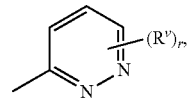 U-43
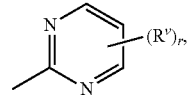 U-44
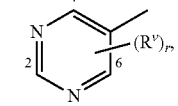 U-45
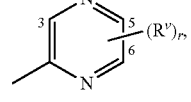 U-46
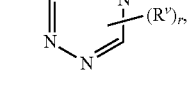 U-47
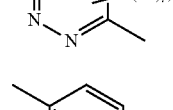 U-48
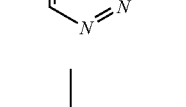 U-49
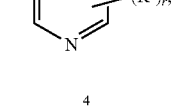 U-50
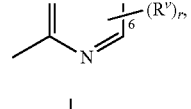 U-51
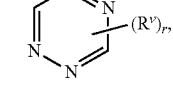 U-52
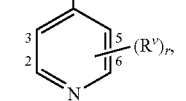 U-53
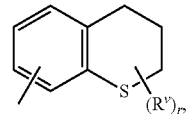 U-54

-continued
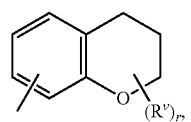 U-55
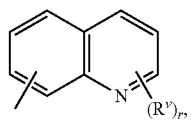 U-56
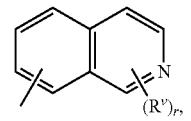 U-57
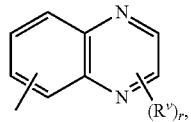 U-58
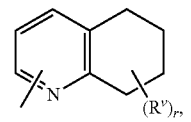 U-59
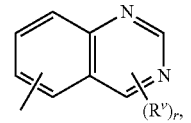 U-60
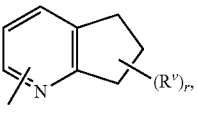 U-61
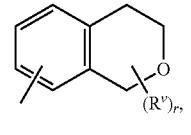 U-62
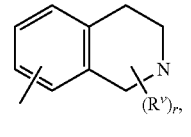 U-63
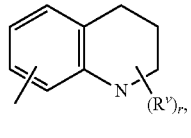 U-64
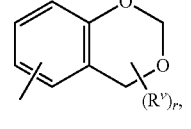 U-65
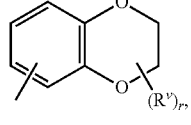 U-66
-continued
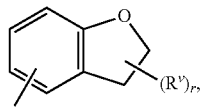 U-67
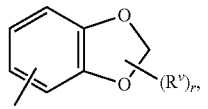 U-68
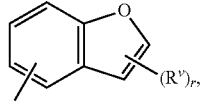 U-69
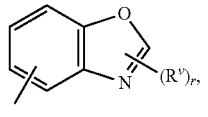 U-70
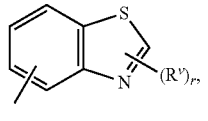 U-71
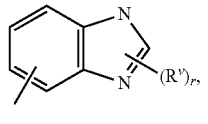 U-72
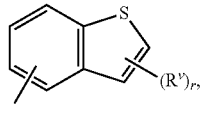 U-73
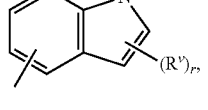 U-74
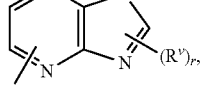 U-75
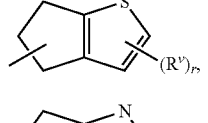 U-76
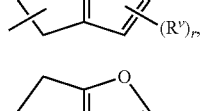 U-77
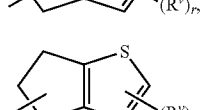 U-78
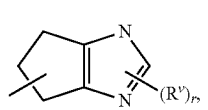 U-79
U-80

-continued

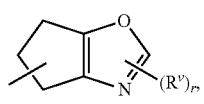 U-81

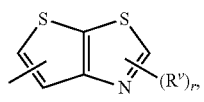 U-82

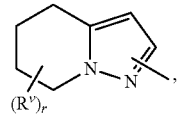 U-83

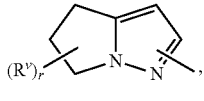 U-84

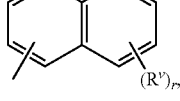 U-85

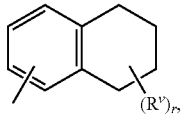 U-86

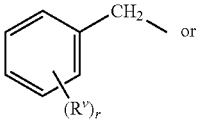 U-87 or

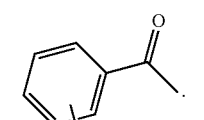 U-88

As indicated above, the carbon moieties L, $R^1$, $R^2$, $R^3$, $R^4$, $R^{10}$ and X may comprise saturated or partially saturated carbocyclic and heterocyclic rings, which can be further optionally substituted. The term "optionally substituted" in connection with these L and R carbon moieties refers to carbon moieties which are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. Examples of saturated or partially saturated carbocyclic rings include optionally substituted $C_3$-$C_8$ cycloalkyl and optionally substituted $C_3$-$C_8$ cycloalkyl. Examples of saturated or partially saturated heterocyclic rings include 5- or 6-membered nonaromatic heterocyclic rings optionally including one or two ring members selected from the group consisting of C(=O), S(O) or S(O)$_2$, optionally substituted. Examples of such L, $R^1$, $R^2$, $R^3$, $R^4$, $R^{10}$ and X carbon moieties include those illustrated as G-1 through G-35 in Exhibit 2. Note that when the attachment point on these G groups is illustrated as floating, the G group can be attached to the remainder of Formulae 1 and 2 through any available carbon or nitrogen of the G group by replacement of a hydrogen atom. The optional substituents can be attached to any available carbon or nitrogen by replacing a hydrogen atom (said substituents are not illustrated in Exhibit 2 since they are optional substituents). Note that when G comprises a ring selected from G-24 through G-31, G-34 and G-35, $Q^2$ may be selected from O, S, NH or substituted N.

Exhibit 2

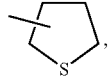 G-1

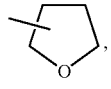 G-2

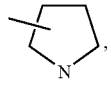 G-3

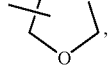 G-4

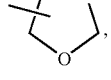 G-5

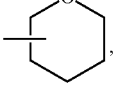 G-6

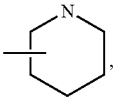 G-7

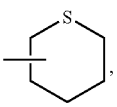 G-8

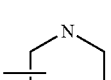 G-9

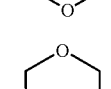 G-10

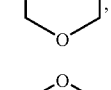 G-11

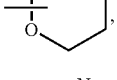 G-12

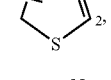 G-13

-continued

G-14 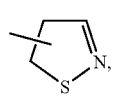

G-15 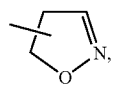

G-16 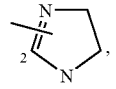

G-17 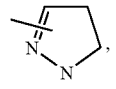

G-18 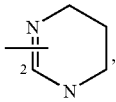

G-19 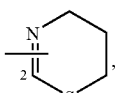

G-20 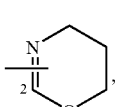

G-21 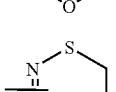

G-22 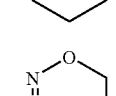

G-23 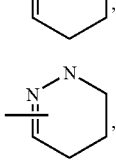

G-24 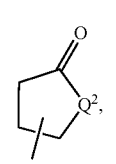

G-25 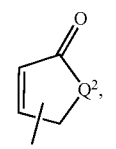

G-26 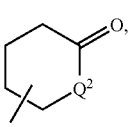

G-27 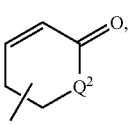

-continued

G-28 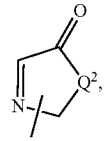

G-29 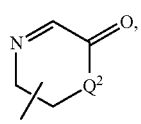

G-30 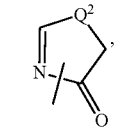

G-31 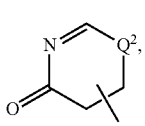

G-32 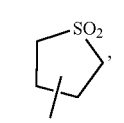

G-33 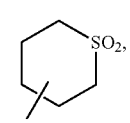

G-34 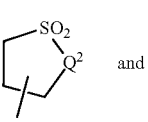 and

G-35 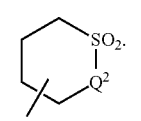

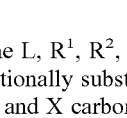

It is noted that the L, $R^1$, $R^2$, $R^3$, $R^4$, $R^{10}$ and X carbon moieties may be optionally substituted. As noted above, L, $R^1$, $R^2$, $R^3$, $R^4$, $R^{10}$ and X carbon moieties may commonly comprise, among other groups, a U group or a G group further optionally substituted with from one to four substituents. Thus the L, $R^1$, $R^2$, $R^3$, $R^4$, $R^{10}$ and X carbon moieties may comprise a U group or a G group selected from U-1 through U-88 or G-1 through G-35, and further substituted with additional substituents including one to four U or G groups (which may be the same or different) with both the core U or G group and substituent U or G groups optionally further substituted. Of particular note are L carbon moieties comprising a U group optionally substituted with from one to three additional substituents. For example, L can be the group U-41.

Embodiments of the present invention include:

Embodiment 1

The method for preparing the compound of Formula 1 wherein the molar ratio of bromine to the compound of Formula 2 is in a ratio of about 3:1 to about 1:1.

Embodiment 2

The method of Embodiment 1 wherein the molar ratio of bromine to the compound of Formula 2 is about 2:1 to about 1:1.

Embodiment 3

The method of Embodiment 2 wherein the molar ratio of bromine to the compound of Formula 2 is about 1.5:1 to about 1:1.

Embodiment 4

The method for preparing the compound of Formula 1 wherein the bromine is added as a gas to the compound of Formula 2.

Embodiment 5

The method of Embodiment 4 wherein the gaseous bromine is diluted with an inert gas.

Embodiment 6

The method of Embodiment 5 wherein the inert gas is nitrogen.

Embodiment 7

The method of Embodiment 5 wherein the molar ratio of the inert gas to the bromine is about 50:1 to 2:1.

Embodiment 8

The method of Embodiment 7 wherein the molar ratio of the inert gas to the bromine is about 30:1 to 4:1.

Embodiment 9

The method for preparing the compound of Formula 1 wherein the temperature is above about 100° c.

Embodiment 10

The method of Embodiment 9 wherein the temperature is above about 120° C.

Embodiment 11

The method for preparing the compound of Formula 1 wherein the temperature is below about 180° C.

Embodiment 12

The method of Embodiment 11 wherein the temperature is below about 150° C.

Embodiment 13

The method of Embodiment 12 wherein the temperature is below about 140° C.

Embodiment 14

The method for preparing the compound of Formula 1 wherein a base is combined with the compound of Formula 2 either before or after contacting with the bromine.

Embodiment 15

The method of Embodiment 14 wherein the base is selected from tertiary amines (including optionally substituted pyridines) and inorganic bases.

Embodiment 16

The method of Embodiment 15 wherein the base is calcium carbonate and the amount of the base is about 0 to 10.0 equivalents relative to the bromine.

Embodiment 17

The method of Embodiment 16 wherein the amount of the base is about 0 to 4.0 equivalents relative to the bromine.

Embodiment 18

The method of Embodiment 15 wherein the amount of the base is about 0 to 2.4 equivalents relative to the bromine.

Embodiment 19

The method for preparing the compound of Formula 1 wherein a solvent is combined with the compound of Formula 2 to form a mixture before contacting with bromine.

Embodiment 20

The method of Embodiment 19 wherein the solvent is an optionally halogenated hydrocarbon with a boiling point higher than 100° C.

Embodiment 21

The method of Embodiment 20 wherein the solvent is an optionally chlorinated aromatic hydrocarbon or dibromoalkane.

Embodiment 22

The method of Embodiment 21 wherein the solvent is t-butylbenzene, chlorobenzene or 1,2-dibromoethane.

Embodiment 23

The method of Embodiment 22 wherein the solvent is t-butylbenzene.

Embodiment 24

The method of Embodiment 22 wherein the solvent is chlorobenzene.

Embodiment 24b

The method of any one of Embodiments 19-24 wherein the temperature is about the boiling point of the solvent.

Embodiment 25

The method for preparing the compound of Formula 1 wherein the molar equivalents of solvent relative to the compound of Formula 2 is about 5:1 to 50:1.

Embodiment 26

The method of Embodiment 25 wherein the molar equivalents of solvent relative to the compound of Formula 2 is about 8:1 to 40:1.

Embodiment 27

The method of Embodiment 26 wherein the molar equivalents of solvent relative to the compound of Formula 2 is about 10:1 to 30:1.

Embodiment 28

The method for preparing the compound of Formula 1 wherein X is halogen, $OR^3$ or an optionally substituted carbon moiety.

Embodiment 29

The method of Embodiment 28 wherein X is halogen or $C_1$-$C_4$ haloalkyl.

Embodiment 30

The method of Embodiment 29 wherein X is Br or $CF_3$.

Embodiment 31

The method of Embodiment 30 wherein X is Br.

Embodiment 32

The method of Embodiment 28 wherein X is $OR^3$.

Embodiment 33

The method of Embodiment 32 wherein $R^3$ is H or $C_1$-$C_4$ haloalkyl.

Embodiment 34

The method of Embodiment 33 wherein $R^3$ is $CF_2H$ or $CH_2CF_3$.

Embodiment 35

The method of Embodiment 32 wherein $R^3$ is H.

Embodiment 36

The method for preparing the compound of Formula 1 wherein L is a phenyl ring or a 5- or 6-membered heteroaromatic ring, optionally substituted with 1 to 3 $R^5$.

Embodiment 37

The method of Embodiment 36 wherein L is pyridinyl or phenyl, optionally substituted with 1 to 3 $R^5$; and each $R^5$ is independently halogen or $C_1$-$C_4$ haloalkyl.

Embodiment 38

The method of Embodiment 37 wherein L is

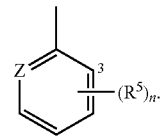

Embodiment 39

The method of Embodiment 38 wherein Z is N or $CR^9$; and $R^9$ is H, halogen or $C_1$-$C_4$ haloalkyl.

Embodiment 40

The method of Embodiment 39 wherein Z is N.

Embodiment 41

The method of Embodiment 40 wherein each $R^5$ is independently halogen or $CF_3$.

Embodiment 42

The method of Embodiment 41 wherein the ring is substituted at the 3-position with an $R^5$ being halogen.

Embodiment 43

The method of Embodiment 42 wherein n is 1.

Embodiment 44

The method of Embodiment 43 wherein $R^5$ is Br or Cl.

Embodiment 45

The method of Embodiment 39 wherein Z is $CR^9$.

Embodiment 46

The method of Embodiment 45 wherein $R^9$ is H, halogen or $CF_3$.

Embodiment 47

The method of Embodiment 46 wherein $R^9$ is halogen.

Embodiment 48

The method of Embodiment 47 wherein $R^9$ is Br or Cl.

Embodiment 49

The method for preparing the compound of Formula 1 wherein $R^1$ is H or $C_1$-$C_4$ alkyl.

Embodiment 50

The method of Embodiment 49 wherein $R^1$ is H.

Embodiment 51

The method for preparing the compound of Formula 1 wherein $R^2$ is H, CN, $C_1$-$C_4$ alkyl, $CO_2R^{10}$, $NO_2$ or $SO_2R^4$; and $R^{10}$ is H or $C_1$-$C_4$ alkyl.

Embodiment 52

The method of Embodiment 51 wherein $R^2$ is $CO_2R^{10}$.

Embodiment 53

The method of Embodiment 52 wherein $R^{10}$ is H or $C_1$-$C_4$ alkyl.

Embodiment 54

The method of Embodiment 53 wherein $R^{10}$ is $C_1$-$C_4$ alkyl.

Embodiment 55

The method of Embodiment 54 wherein $R^{10}$ is methyl or ethyl.

Embodiment 56

The method of Embodiment 51 wherein $R^4$ is $C_1$-$C_4$ alkyl or optionally substituted phenyl.

Embodiment 57

The method of Embodiment 56 wherein $R^4$ is methyl, phenyl or 4-tolyl.

Further embodiments include the method for preparing a compound of Formula 3 using a compound of Formula 1a prepared by the method of any of Embodiments 1-57.

Of note are the following embodiments:

Embodiment A

The method for preparing the compound of Formula 1 wherein
X is halogen, $OR^3$ or $C_1$-$C_4$ haloalkyl;
L is a phenyl ring or a 5- or 6-membered heteroaromatic ring, optionally substituted with 1 to 3 $R^5$;
$R^1$ is H;
$R^2$ is H, CN, $C_1$-$C_4$ alkyl, $CO_2R^{11}$, $NO_2$ or $SO_2R^4$;
$R^3$ is H or $C_1$-$C_4$ haloalkyl;
$R^4$ is $C_1$-$C_4$ alkyl or optionally substituted phenyl;
each $R^5$ is independently halogen or $C_1$-$C_4$ haloalkyl; and
$R^{10}$ is H or $C_1$-$C_4$ alkyl.

Embodiment B

The method of Embodiment A wherein the compound of Formula 1 is of Formula 1a

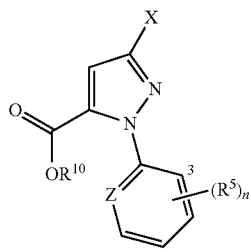

and the compound of Formula 2 is of Formula 2a

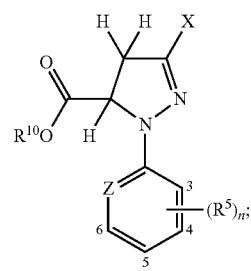

Z is N or $CR^9$;
$R^9$ is H, halogen or $C_1$-$C_4$ haloalkyl; and
n is an integer from 0 to 3.

Embodiment C

The method of Embodiment B wherein
X is Br or $CF_3$;
Z is N;
each $R^5$ is independently halogen or $CF_3$; and
$R^{10}$ is methyl or ethyl.

Embodiment D

The method of Embodiment B wherein
X is $OR^3$;
$R^3$ is H or $C_1$-$C_4$ haloalkyl; and
$R^{10}$ is H or $C_1$-$C_4$ alkyl.

Embodiment E

The method of Embodiment D wherein
X is OH, $OCF_2H$ or $OCH_2CF_3$;
Z is N;
each $R^5$ is independently halogen or $CF_3$; and
$R^{10}$ is methyl or ethyl.

Embodiment F

The method for preparing the compound of Formula 1 wherein the temperature is between about 120° C. and 140° C.

Embodiment G

The method for preparing the compound of Formula 1 wherein a base is combined with the compound of Formula 2 either before or after contacting with the bromine and the molar equivalents of base relative to bromine is about 0:1 to 4:1.

Embodiment H

The method for preparing the compound of Formula 1 wherein the molar equivalents of bromine relative to the compound of Formula 2 is about 2:1 to 1:1.

Embodiment I

The method for preparing the compound of Formula 1 wherein a solvent is combined with the compound of Formula 2 to form a mixture before contacting with bromine and the temperature is about the boiling point of the solvent.

Embodiment J

The method for preparing the compound of Formula 1 wherein the bromine is added as a gas to the compound of Formula 2 and the gaseous bromine is diluted with an inert gas.

Embodiment K

The method of preparing a compound of Formula 3

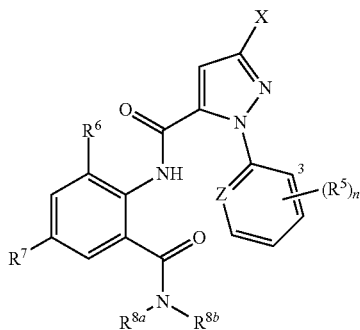

wherein

X is halogen, $OR^3$ or $C_1$-$C_4$ haloalkyl;

Z is N or $CR^9$;

$R^3$ is H or $C_1$-$C_4$ haloalkyl;

each $R^5$ is independently halogen or $C_1$-$C_4$ haloalkyl;

$R^6$ is $CH_3$, F, Cl or Br; and $R^7$ is F, Cl, Br, I, CN or $CF_3$;

$R^{8a}$ is $C_1$-$C_4$ alkyl;

$R^{8b}$ is H or $CH_3$;

$R^9$ is H, halogen or $C_1$-$C_4$ haloalkyl; and n is an integer from 0 to 3 using a compound of Formula 1a

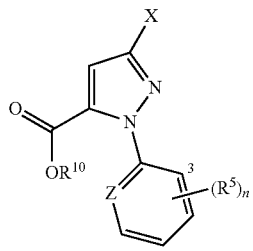

wherein $R^{10}$ is H or $C_1$-$C_4$ alkyl;
the method characterized by preparing the compound of Formula 1a by the method of Embodiment B.

Embodiment L

The method of Embodiment K wherein
Z is N;
each $R^5$ is independently Cl, Br or $CF_3$;
one $R^5$ is at the 3-position; and
$R^{10}$ is methyl or ethyl.

Embodiment M

The method of Embodiment L wherein X is Br; n is 1; and $R^5$ is Cl.

As illustrated in Comparative Example 1, attempts to oxidize 2-pyrazolines of Formula 2 to pyrazoles of Formula 1 using bromine as the oxidant at temperature near ambient conditions frequently result in side reactions involving bromination of a substituent on the pyrazoline or pyrazole ring. It has been discovered that contacting a 2-pyrazoline of Formula 2 with bromine at about 80° C. or above can provide with excellent selectivity the corresponding pyrazole of Formula 1 as shown in Scheme 1.

Scheme 1

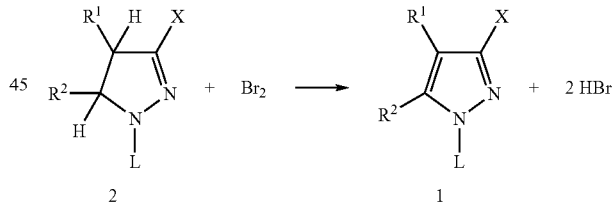

The reaction is carried out by contacting the 2-pyrazoline of Formula 2, typically as a solution in an inert solvent, with bromine at elevated temperature. By-product hydrogen bromide is removed either chemically, for example by addition of an appropriate base, or physically, for example by sparging the reaction mass with an inert gas. After the reaction is complete, the product is isolated by methods known to those skilled in the art, for example, crystallization or distillation.

The process can be conducted in a variety of inert solvents, preferably of low to moderate polarity. Suitable solvents include aliphatic hydrocarbons, halocarbons, aromatics and mixtures of the foregoing. Aliphatic hydrocarbon solvents include straight chain or branched alkanes such as octane, nonane, decane, and the like, as well as mixtures of aliphatic hydrocarbons, such as mineral spirits and ligroin. Halocarbon solvents include straight chain or branched alkanes substituted by at least one halogen, such as 1,1,2,2-tetrachloroethane, 1,2-dibromoethane, and the like. Aromatic solvents include benzene optionally substituted with one or more substituents selected from halogen, tertiary alkyl, and straight chain or branched alkyl fully substituted with halogen on the carbon atom connecting to the benzene ring and optionally substituted with halogen on other carbon atoms, such as benzene, tert-butylbenzene, chlorobenzene, 1,2-dichlorobenzene, benzotrifluoride, benzotrichloride and the like. The optimum choice of solvent depends upon the desired temperature and pressure of operation. If desired, the process may be conducted at greater than ambient pressures in order to elevate the boiling point of the solvent. Reduced pressure may also be used. For ease of operation, however, the preferred operating pressure is ambient, in which case the boiling point of the solvent must be equal to or greater than the desired operating temperature. One embodiment of the present invention is the solvent is an optionally halogenated hydrocarbon with a boiling point higher than 100° C. Particularly suitable solvents include t-butylbenzene, chlorobenzene and 1,2-dibromoethane. The molar ratio of solvent to the compound of Formula 2 is typically about 50:1 to 5:1, preferably about 40:1 to 8:1, and most preferably about 30:1 to 10:1.

According to the present invention, the reaction temperature should be elevated to a level at which oxidation is favored over the competing bromination to maximize process yield. In one embodiment of the process of the present invention, reaction temperatures are typically in the range of about 80° C. to 180° C. In additional embodiments, temperatures are in the range of about 100° C. to 150° C., and about 120° C. to 140° C.

In the present invention, the oxidant bromine can be added either as a liquid or a gas. In one embodiment, gaseous bromine may be diluted with an inert gas such as nitrogen, helium, argon, or the like. The bromine can be added over as short a period as hydrogen bromide removal allows. In one embodiment, for practical purposes, the addition time of bromine is typically between 0.5 to 20 hours, preferably between 0.5 to 10 hours, and most preferably between 1.5 to 4 hours. Although a wide range of reactant ratios is possible, the nominal mole ratio of the bromine to the Formula 2 compound is typically from about 3 to 1, preferably about 2 to 1, and most preferably about 1.5 to 1.

As the reaction of the present method generates hydrogen bromide as a byproduct, which would otherwise bind to the basic centers on the compounds of Formulae 1 and 2, or interfere with the oxidation reaction, the method is typically conducted by removing the hydrogen bromide from the solution chemically by addition of a suitable inorganic or organic base and/or sparging with an inert gas and/or heating at reflux. Various inorganic bases can be used, including alkali or alkaline earth oxides or carbonates, such as sodium carbonate, potassium carbonate, calcium carbonate, calcium oxide, or the like. Various organic bases can be used, including trisubstituted amines, such as triethylamine, N,N-diisopropylethylamine, N,N-diethylaniline or the like, or heteroaromatic bases such as pyridine, picoline, imidazole or the like. In one embodiment of the present invention, calcium carbonate is a suitable base for reasons of cost and availability. The base is typically added before the addition of the bromine. As shown in Scheme 1, the generation of every mole equivalent of pyrazole 1 produces 2 mole equivalents of by-product hydrogen bromide. Therefore, at least 2 mole equivalents of base versus every mole of the compound of Formula 2 are required to neutralize the by-product hydrogen bromide. Excess base may be used within the bounds of economic feasibility. One embodiment of the nominal mole equivalent ratio of inorganic bases charged to the bromine charged is about 2 to 10. Another embodiment of the nominal mole equivalent ratio of organic bases charged to the bromine charged is about 2 to 4.

By-product hydrogen bromide can also be removed from the reaction mass by physical means, for example by sparging the solution with inert gas or heating at reflux. Embodiments of suitable inert gases include nitrogen, helium, argon and carbon dioxide. The inert gas can be mixed with the bromine prior to introduction to the reactor. The amount of inert gas should be sufficient to efficiently remove the hydrogen bromide at the rate it is produced. The amount of inert gas required depends upon the solvent, reaction temperature and bromine addition rate. In one embodiment of the present invention, the nominal molar ratio of inert gas versus bromine is typically about 50:1 to 2:1, and the inert gas is added over the same period of time as the addition of bromine. In an additional embodiment the nominal molar ratio of inert gas versus bromine is about 30:1 to 4:1. When heating at the reflux temperature of the reaction solvent, the vaporized solvent itself can function as an inert gas for removal of hydrogen bromide. In one embodiment the nominal molar ratio of the vaporized solvent versus bromine is above about 5 during the course of bromine addition. In an additional embodiments, the ratio is above about 10 and below about 50 of the vaporized solvent versus bromine during the course of bromine addition.

According to the process of the present invention, when by-product hydrogen bromide is removed from the reaction mass by sparging the solution with inert gas or heating at reflux, the molar ratio of base present in the reaction mixture versus bromine can be less than 2:1. The nominal mole ratio of the base added to the reaction mixture versus bromine is typically from about 0 to 10, preferably from about 0 to 4, and most preferably from about 0 to 2.4.

According to the present invention, the solvent is typically combined with the compound of Formula 2 to form a mixture and is heated at reflux before contacting with bromine. As the bromine is added to the reaction mixture, the reaction by-product hydrogen bromide is removed by concurrently sparging the reaction mixture with an inert gas and heating at reflux; the reaction temperature is thus about the boiling point of the solvent. Therefore in an embodiment according to the present invention, the solvent is combined with the compound of Formula 2 to form a mixture before contacting with bromine, and the reaction temperature is about the boiling point of the solvent.

The reaction is typically complete within one hour to one day; the progress of the reaction can by monitored by such techniques known to those skilled in the art as thin layer chromatography and analysis of the $^1$H NMR spectrum. The product pyrazoles of Formula 1 can be isolated from the reaction mixture by methods known to those skilled in the art, including extraction, crystallization and distillation.

As shown in Scheme 2, Formula 1a is a subgenus of Formula 1 wherein X, $R^5$, $R^{10}$ and Z are as previously defined. Compounds of Formula 1a can be prepared from corresponding compounds of Formula 2a, which is a subgenus of Formula 2, by the method of the present invention as previously described.

Scheme 2

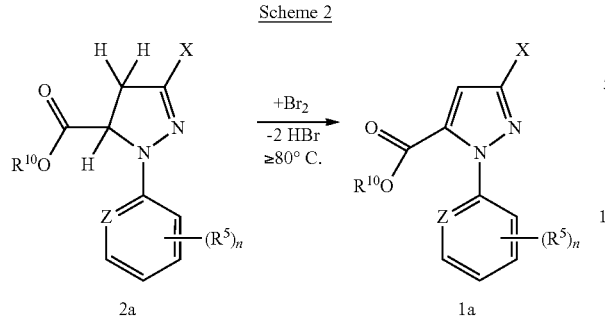

Compounds of Formula 2 can be prepared by the great variety of modern synthetic methodologies known to those skilled in the art. In general, compounds of Formula 2 wherein X is a carbon moiety can be prepared from reactions of α,β-unsaturated ketones of Formula 4 and hydrazines of Formula 5 as outlined in Scheme 3.

Scheme 3

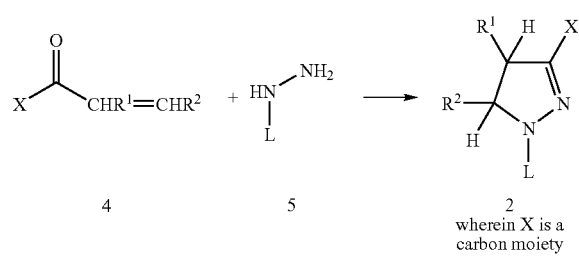

Compounds of Formula 2b can be prepared by contacting compounds of Formula 4a with hydrazines of Formula 5 (Scheme 4). Compounds of Formula 2b can then be alkylated with an alkylating agent Lg-$R^3$ of Formula 6 in the presence of a suitable base to yield compounds of Formula 2c. The alkylation reaction is generally conducted in a solvent, which can comprise ethers, such as tetrahydrofuran or dioxane, and polar aprotic solvents, such as acetonitrile, N,N-dimethylformamide, and the like. The base can be selected from inorganic bases such as potassium carbonate, sodium hydroxide or sodium hydride. Preferably the reaction is conducted using potassium carbonate with N,N-dimethylformamide or acetonitrile as the solvent. In the alkylating agent Lg-$R^3$, Lg is a nucleofuge (i.e. leaving group) such as halogen (e.g., Br, I), $OS(O)_2CH_3$ (methanesulfonate), $OS(O)_2CF_3$, $OS(O)_2Ph-p-CH_3$ (p-toluenesulfonate), and the like. The product of Formula 2c can be isolated by conventional techniques such as extraction.

Scheme 4

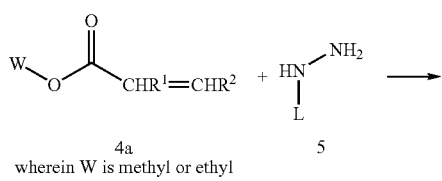

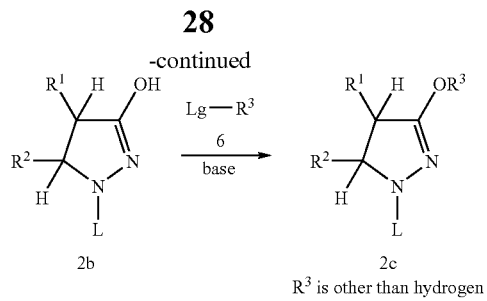

As outlined in Scheme 5, compounds of Formula 2d wherein X is halogen can be prepared from the corresponding compounds of Formula 2b by halogenation.

Scheme 5

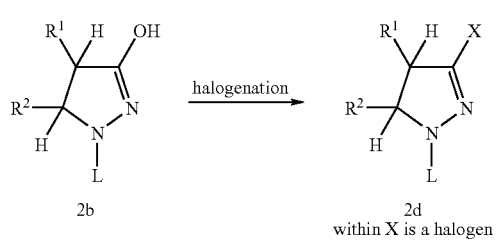

Halogenating reagents that can be used include phosphorus oxyhalides, phosphorus trihalides, phosphorus pentahalides, thionyl chloride, dihalotrialkylphosphoranes, dihalotriphenylphosphoranes, oxalyl chloride and phosgene. Preferred are phosphorus oxyhalides and phosphorus pentahalides. Typical solvents for this halogenation include halogenated alkanes such as dichloromethane, chloroform, chlorobutane and the like, aromatic solvents such as benzene, xylene, chlorobenzene and the like, ethers such as tetrahydrofuran, p-dioxane, diethyl ether and the like, and polar aprotic solvents such as acetonitrile, N,N-dimethylformamide and the like. Optionally, an organic base, such as triethylamine, pyridine, N,N-dimethylaniline or the like, can be added. Addition of a catalyst, such as N,N-dimethylformamide, is also an option.

Alternatively, compounds of Formula 2d wherein X is halogen can be prepared by treating the corresponding compounds of Formula 2d wherein X is a different halogen (e.g., Cl for making Formula 2d wherein X is Br), with hydrogen bromide or hydrogen chloride, respectively. By this method the X halogen substituent on the Formula 2d starting compound is replaced with Br or Cl from hydrogen bromide or hydrogen chloride, respectively. Starting compounds of Formula 2d wherein X is Cl or Br can be prepared from corresponding compounds of Formula 2b as already described.

For general references to the preparation of 2-pyrazolines see Levai A., *J. Heterocycl. Chem.* 2002, 39(1), pp 1-13; El-Rayyes, N. R.; Al-Awadi N. A., *Synthesis* 1985, 1028-22 and references cited within. As Formula 2a is a subgenus of Formula 2 wherein X, $R^5$, $R^{10}$ and Z are as previously defined, compounds of Formula 2a can be prepared by the methods already described previously in Schemes 3, 4 and 5. For additional references to the preparation of compounds of Formula 2a see PCT publications WO 2003/016283 and WO 2004/011453.

It is recognized that some reagents and reaction conditions described above for preparing compounds of Formula 2 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 2. One skilled in the art will also recognize that it may be necessary to perform a combination of the steps illustrated in the above schemes in an order other than that implied by the particular sequence presented to prepare the compounds of Formula 2. One skilled in the art will also recognize that compounds of Formula 2 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are focused on the bromination of 3-bromo-1-(3-chloro-2-pyridinyl)-4,5-dihydro-1H-pyrazole-5-carboxylate as outlined in Scheme 6. There are three possible products (Formulae 8, 9 and 10) when bromine is used as oxidant for the oxidation of the 2-pyrazoline of Formula 7. These Examples are to be construed as merely illustrative and not limiting of the disclosure in any way whatsoever.

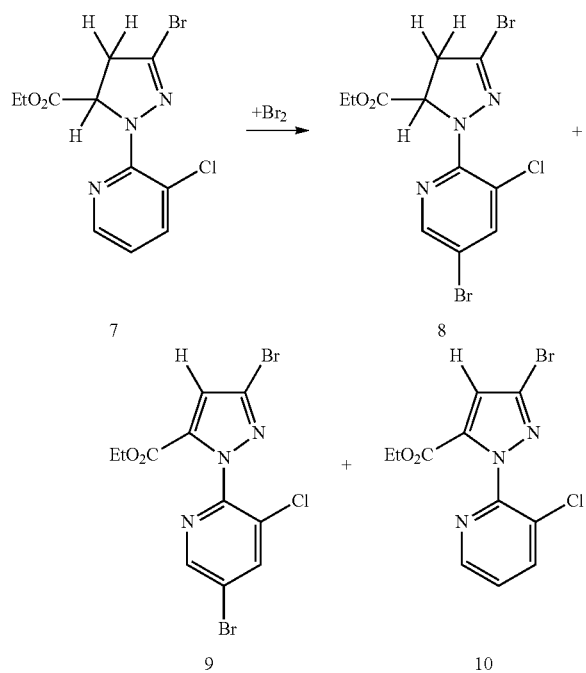

Scheme 6

HPLC means high pressure liquid chromatography. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

Comparative Example 1

Bromination of 3-bromo-1-(3-chloro-2-pyridinyl)-4,5-dihydro-1H-pyrazole-5-carboxylate near ambient temperature A 2-L four-necked flask equipped with a mechanical stirrer, thermometer, addition funnel, reflux condenser, and nitrogen inlet was charged with 50.0 g (0.150 mol) of ethyl 3-bromo-1-(3-chloro-2-pyridinyl)-4,5-dihydro-1H-pyrazole-5-carboxylate (for preparation, see WO 2003/16283, Example 9), 500 mL of dichloromethane, 200 mL of water and 15.0 g (0.179 mol) of sodium bicarbonate. The two-phase mixture was treated dropwise over a period of about 20 minutes with 25.0 g (0.156 mol) of bromine dissolved in 25 mL of dichloromethane. The temperature of the reaction mass rose from 19 to 25° C., and gas evolved rapidly during the addition. The resulting orange mixture was held under ambient conditions for 1 hour. The reaction mass was transferred to a separatory funnel. The dichloromethane layer was separated, dried over magnesium sulfate, filtered, and then concentrated on a rotary evaporator. The resulting brown oil (59.9 g) was found to contain, as determined by $^1$H NMR, ethyl 3-bromo-1-(5-bromo-3-chloro-2-pyridinyl)-4,5-dihydro-1H-pyrazole-5-carboxylate (91% by weight, Formula 8), along with ethyl 3-bromo-1-(5-bromo-3-chloro-2-pyridinyl)-1H-pyrazole-5-carboxylate (2%, Formula 9), ethyl 3-bromo-1-(3-chloro-2-pyridinyl)-1H-pyrazole-5-carboxylate (2%, Formula 10) and dichloromethane (5%).

Formula 8 Compound:
$^1$H NMR (DMSO-d$_6$) δ 8.25 (d, 1H), 8.16 (d, 1H), 5.16 (dd, 1H), 4.11 (q, 2H), 3.61 (dd, 1H), 3.31 (dd, 1H), 1.15 (t, 3H).

Formula 9 Compound:
$^1$H NMR (DMSO-d$_6$) δ 8.76 (d, 1H), 8.73 (d, 1H), 7.37 (s, 1H), 4.18 (q, 2H), 1.12 (t, 3H).

Formula 10 Compound:
$^1$H NMR (DMSO-d$_6$) δ 8.59 (d, 1H), 8.39 (d, 1H), 7.72 (dd, 1H), 7.35 (s, 1 μl), 4.16 (q, 2H), 1.09 (t, 3H).

Example 1

Bromination of ethyl 3-bromo-1-(3-chloro-2-pyridinyl)-1H-pyrazole-5-carboxylate in the presence of pyridine A: Apparatus for Gaseous Addition of Bromine The experimental apparatus for Examples 1A-1C comprised a flow meter, a syringe pump, a mixing chamber, a trap, a scrubber, and a 2-neck 10-mL flask fitted with on one neck with a water-cooled condenser and a Teflon®-coated thermocouple with wires passing up through the condenser to a gauge. The mixing chamber allowed mixing bromine with nitrogen gas before their introduction into the 2-neck flask, which served as the reaction vessel. The mixing chamber consisted of a 7 mL glass vial capped with rubber septum. Nitrogen gas passes through the flow meter and Teflon® fluoropolymer tubing (1.6 mm O.D.) piercing the rubber septum of the mixing chamber. The bromine was injected from a syringe pump into the mixing chamber through a syringe needle piercing the rubber septum of the mixing chamber. The mixture of bromine and nitrogen passed out the mixing chamber through Teflon® tubing piercing the rubber septum and flowed through the tubing piercing a rubber septum on the other neck of the 2-neck flask such that the end of the tubing was submerged below the surface of the reaction solution. The reaction flask was heated using an oil bath, and the reaction temperature was monitored by the thermocouple gauge. Tubing connected to the top of the condenser conducted the effluent nitrogen gas and uncondensed vapor to a trap and then to a scrubber containing aqueous sodium bisulfite solution to trap byproduct hydrogen bromide and any excess bromine.

Example 1A

In the Presence of Pyridine

Into the two-neck flask in the above described apparatus was added 0.500 g (1.503 mmol) of ethyl 3-bromo-1-(3-chloro-2-pyridinyl)-4,5-dihydro-1H-pyrazole-5-carboxylate, 0.256 g (3.23 mmol) of pyridine and 5.05 g of chlorobenzene and heated to 115° C. Bromine (0.265 g, 85 µL, 1.66 mmol) was injected from the syringe into the mixing chamber over 2 h (i.e., 40 µL/h) while nitrogen was flowed through the mixing chamber into the reaction mixture at a rate of 0.41 mL/s. The nitrogen flow was continued for another half hour. The orange colored reaction mixture was cooled and then analyzed by quantitative HPLC using O-terphenyl (61.4 mg) as internal standard. Analytic samples for HPLC analysis were prepared by adding weighed O-terphenyl to the reaction mixture, and 5 mL of dimethylsulfoxide to dissolve all precipitated salts. A 20 µL aliquot of the resulting solution was withdrawn and diluted with 1 mL of acetonitrile and filtered through a 0.2 µm frit to give the HPLC analytical sample. The yield is reported in mole %. HPLC showed the resulting solution other than chlorobenzene and pyridine to contain 89% of ethyl 3-bromo-1-(5-bromo-3-chloro-2-pyridinyl)-1H-pyrazole-5-carboxylate (Formula 10) and 9% of ethyl 3-bromo-1-(3-chloro-2-pyridinyl)-4,5-dihydro-1H-pyrazole-5-carboxylate (Formula 7).

Example 1B

In the Presence of Calcium Carbonate

Into the two-neck 10 mL flask in the above described apparatus also equipped with a stir bar to facilitate stirring was added 0.500 g (1.507 mmol) of ethyl 3-bromo-1-(3-chloro-2-pyridinyl)-4,5-dihydro-1H-pyrazole-5-carboxylate, 0.507 g (5.06 mmol) of calcium carbonate and 5.00 g of chlorobenzene and heated to 130° C. Bromine (0.265 g, 85 µL, 1.66 mmol) was injected from the syringe into the mixing chamber over 2 h (40 µL/h) while nitrogen was flowed through the mixing chamber into the stirred reaction mixture at a rate of 0.41 mL's. The nitrogen flow was continued for another 10 minutes. The reaction mixture was cooled and then analyzed by quantitative HPLC using O-terphenyl (51.1 mg) as internal standard. HPLC showed the resulting solution other than chlorobenzene to contain 96% of ethyl 3-bromo-1-(5-bromo-3-chloro-2-pyridinyl)-1H-pyrazole-5-carboxylate (Formula 10) and 2% of ethyl 3-bromo-1-(3-chloro-2-pyridinyl)-4,5-dihydro-1H-pyrazole-5-carboxylate (Formula 7).

Example 1C

With Nitrogen Sparse and No Added Base

Into the two-neck flask of the above described apparatus was added 0.25 g (0.76 mmol) of ethyl 3-bromo-1-(3-chloro-2-pyridinyl)-4,5-dihydro-1H-pyrazole-5-carboxylate and 2.5 g of chlorobenzene and heated to 130° C. Bromine (0.233 g, 75 µL, 1.46 mmol) was injected from the syringe into the mixing chamber over 3 h (15 µL/h) while nitrogen was continuously flowed through the mixing chamber into the reaction mixture at a rate of 0.46 mL/s. The reaction mixture was cooled and then analyzed by quantitative HPLC using O-terphenyl (32.7 mg) as internal standard. HPLC showed the resulting solution other than chlorobenzene to contain 88% of ethyl 3-bromo-1-(5-bromo-3-chloro-2-pyridinyl)-1H-pyrazole-5-carboxylate (Formula 10) and 0% of ethyl 3-bromo-1-(3-chloro-2-pyridinyl)-4,5-dihydro-1H-pyrazole-5-carboxylate (Formula 7).

Example 3

Bromination of ethyl 3-bromo-1-(3-chloro-2-pyridinyl)-4,5-dihydro-1H-pyrazole-5-carboxylate under various reaction conditions The following general procedure was used for Examples 3-1 to 3-38. A flat-bottomed cylindrical glass vessel (15 mm I.D. by 80 mm) was charged with ethyl 5-bromo-2-(3-chloro-2-pyridinyl)-4,5-dihydro-1H-pyrazole-5-carboxylate, chlorobenzene and optionally calcium carbonate. The glass vessel was then equipped with a magnetic stirring bar, a water-cooled condenser, and a Teflon®-coated thermocouple for measuring temperature. The reaction mixture was heated to the desired temperature with an oil bath, and a nitrogen stream at a particular flow rate was passed through a Teflon® tube inserted into the reaction mixture. The bromine was added at a controlled rate from a syringe attached to a syringe pump; the syringe was connected via a T-connector to the Teflon® tubing that carried the nitrogen stream, and in this way bromine was carried in the vapor phase into the reaction mixture. The exit gases were passed through a water trap that was used to collect hydrogen bromide and any excess bromine that passed through the reaction mixture. After all the bromine had been added, the reaction mixture was cooled, while continuing the nitrogen flow. The reaction mixture was prepared for analysis by addition of a weighed amount of dimethylsulfoxide (4.3-4.4 g) containing a known amount of ortho-terphenyl as an internal standard. After thorough mixing, a 7.5 to 15 µL aliquot of this mixture was diluted with 900 µL of acetonitrile, and was passed through a 0.2 micron filter, and analyzed on an Agilent® 1100 series High Pressure Liquid Chromatography instrument. The amount of compound of Formula 7, moles of solvent (chlorobenzene) and bromine relative to starting compound of Formula 7, addition rate of bromine, mole equivalents of base (calcium carbonate) and nitrogen relative to bromine, the nitrogen flow rate, reaction temperature, and reaction results including % of conversion of starting compound of Formula 7 and % yields of compounds of Formulae 10, 9 and 8 are listed in Table 1 for each example. The reaction yield of each compound of the reaction mixture is listed as mol % for each example in Table 1.

TABLE 1

| Ex. | Amount Cpd. 7 (g) | Moles solvent to Cpd 7 | Equiv. CaCO$_3$ to Br$_2$ | Equiv. Br$_2$ to Cpd 7 | Br$_2$ Add'n Rate (μL/h) | Equiv. N$_2$ to Br$_2$ | N$_2$ Flow Rate (mL/min) | Temp. (°C.) | % Conv. of Cpd 7 | Mol % Cpd. 10 | Mol % Cpd. 9 | Mol % Cpd. 8 |
|---|---|---|---|---|---|---|---|---|---|---|---|---|
| 3-1 | 1.00 | 15 | 0.0 | 1.0 | 154 | 3 | 4.0 | 110 | 52.9 | 32.8 | 1.5 | 18.0 |
| 3-2 | 1.00 | 15 | 0.4 | 1.4 | 216 | 2 | 20.0 | 110 | 69.8 | 33.3 | 3.1 | 31.8 |
| 3-3 | 0.67 | 22 | 0.0 | 1.0 | 103 | 5 | 12.0 | 110 | 52.6 | 35.7 | 1.1 | 15.1 |
| 3-4 | 0.67 | 23 | 1.0 | 1.2 | 123 | 4 | 20.0 | 110 | 62.3 | 36.8 | 2.4 | 21.8 |
| 3-5 | 0.50 | 30 | 1.2 | 1.0 | 77 | 7 | 4.0 | 110 | 50.8 | 36.8 | 0.8 | 13.5 |
| 3-6 | 0.50 | 30 | 0.0 | 1.4 | 108 | 5 | 4.0 | 110 | 61.8 | 37.4 | 2.1 | 21.8 |
| 3-7 | 1.00 | 16 | 0.9 | 1.4 | 86 | 6 | 4.0 | 110 | 68.8 | 39.9 | 4.5 | 17.7 |
| 3-8 | 1.00 | 16 | 1.2 | 1.0 | 39 | 13 | 20.0 | 110 | 59.5 | 45.9 | 3.3 | 8.3 |
| 3-9 | 0.50 | 30 | 0.0 | 1.0 | 19 | 26 | 4.0 | 110 | 56.7 | 47.8 | 1.5 | 5.5 |
| 3-10 | 0.50 | 29 | 0.0 | 1.0 | 31 | 16 | 20.0 | 110 | 59.5 | 48.0 | 2.1 | 7.1 |
| 3-11 | 1.00 | 15 | 0.0 | 1.4 | 54 | 9 | 20.0 | 110 | 73.3 | 48.2 | 10.3 | 11.4 |
| 3-12 | 0.67 | 22 | 0.5 | 1.2 | 31 | 16 | 4.0 | 110 | 66.7 | 49.1 | 3.2 | 7.6 |
| 3-13 | 0.50 | 30 | 0.9 | 1.4 | 27 | 19 | 20.0 | 110 | 80.9 | 63.5 | 10.6 | 5.8 |
| 3-14 | 1.00 | 16 | 0.0 | 1.2 | 185 | 3 | 20.0 | 120 | 58.6 | 38.2 | 1.9 | 15.0 |
| 3-15 | 1.00 | 16 | 1.0 | 1.2 | 185 | 3 | 12.0 | 120 | 65.9 | 42.3 | 2.6 | 16.3 |
| 3-16 | 0.50 | 27 | 0.0 | 1.0 | 31 | 16 | 4.0 | 120 | 65.1 | 56.9 | 1.0 | 3.2 |
| 3-17 | 0.50 | 30 | 0.4 | 1.4 | 108 | 5 | 20.0 | 120 | 77.7 | 60.9 | 4.9 | 10.1 |
| 3-18 | 0.67 | 21 | 0.4 | 1.4 | 36 | 14 | 4.0 | 120 | 89.5 | 75.3 | 4.6 | 1.7 |
| 3-19 | 0.67 | 22 | 0.5 | 1.0 | 43 | 12 | 12.0 | 120 | 84.3 | 77.7 | 2.6 | 2.3 |
| 3-20 | 1.00 | 15 | 1.2 | 1.0 | 39 | 13 | 4.0 | 130 | 95.9 | 63.6 | 0.4 | 0.0 |
| 3-21 | 0.50 | 27 | 0.0 | 1.0 | 77 | 7 | 4.0 | 130 | 70.5 | 63.6 | 0.7 | 0.0 |
| 3-22 | 1.00 | 16 | 1.2 | 1.0 | 154 | 3 | 20.0 | 130 | 78.0 | 67.0 | 1.2 | 0.0 |
| 3-23 | 1.00 | 16 | 0.0 | 1.4 | 216 | 2 | 12.0 | 130 | 92.3 | 69.3 | 8.1 | 1.4 |
| 3-24 | 0.50 | 27 | 0.6 | 1.0 | 31 | 16 | 12.0 | 130 | 88.7 | 74.2 | 0.3 | 2.5 |
| 3-25 | 0.50 | 30 | 0.0 | 1.0 | 77 | 7 | 20.0 | 130 | 87.0 | 74.3 | 0.1 | 0.0 |
| 3-26 | 1.00 | 16 | 0.5 | 1.2 | 74 | 7 | 4.0 | 130 | 93.7 | 74.7 | 1.5 | 0.0 |
| 3-27 | 0.50 | 27 | 1.2 | 1.0 | 19 | 26 | 20.0 | 130 | 94.2 | 78.7 | 0.3 | 0.0 |
| 3-28 | 1.00 | 16 | 0.0 | 1.0 | 39 | 13 | 20.0 | 130 | 95.6 | 81.1 | 0.2 | 0.0 |
| 3-29 | 0.67 | 23 | 0.8 | 1.4 | 144 | 4 | 4.0 | 130 | 92.3 | 81.2 | 2.7 | 1.0 |
| 3-30 | 1.00 | 15 | 0.0 | 1.4 | 54 | 9 | 4.0 | 130 | 100.0 | 83.9 | 1.4 | 0.0 |
| 3-31 | 0.50 | 27 | 0.9 | 1.4 | 27 | 19 | 4.0 | 130 | 98.6 | 84.5 | 0.7 | 0.0 |
| 3-32 | 1.00 | 16 | 0.9 | 1.4 | 54 | 9 | 20.0 | 130 | 99.5 | 88.5 | 0.2 | 0.0 |
| 3-33 | 0.50 | 27 | 0.9 | 1.4 | 108 | 5 | 20.0 | 130 | 95.6 | 89.4 | 2.2 | 1.1 |
| 3-34 | 0.67 | 21 | 0.0 | 1.4 | 58 | 9 | 20.0 | 130 | 100.0 | 90.1 | 0.8 | 2.3 |
| 3-35 | 0.50 | 27 | 0.0 | 1.4 | 27 | 19 | 20.0 | 130 | 99.1 | 90.3 | 0.7 | 0.0 |
| 3-36 | 0.59 | 25 | 0.7 | 1.4 | 42 | 12 | 20.0 | 130 | 99.2 | 92.6 | 0.0 | 0.0 |
| 3-37 | 0.60 | 24 | 0.8 | 1.5 | 43 | 12 | 20.0 | 130 | 99.3 | 93.5 | 0.3 | 0.0 |
| 3-38 | 0.59 | 25 | 0.7 | 1.4 | 42 | 12 | 20.0 | 130 | 100.0 | 94.9 | 0.0 | 0.0 |

The following abbreviations are used in the Table 2: t means tertiary, s means secondary, n means normal, i means iso, Me means methyl, Et means ethyl, Pr means propyl, i-Pr means isopropyl, and Bu means butyl. Table 2 illustrates particular transformations to prepare compounds of Formula 1a from compounds of Formula 2a according to the method of the present invention.

TABLE 2

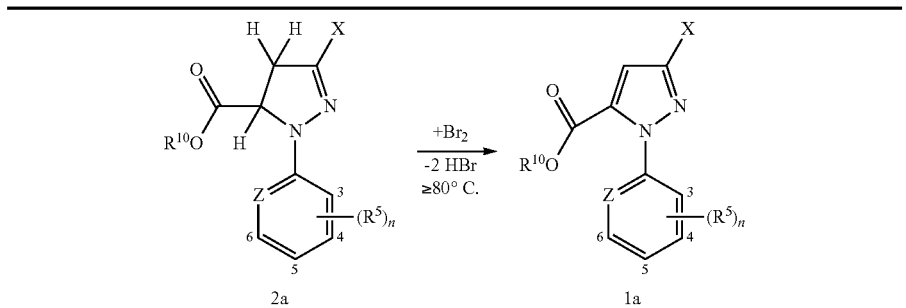

| X is Cl | | | | | | | | | | | | | | | |
|---|---|---|---|---|---|---|---|---|---|---|---|---|---|---|---|
| Z is N | | | | Z is CH | | | | Z is CCl | | | | Z is CBr | | | |
| (R$^5$)$_n$ | R$^{10}$ | (R$^5$)$_n$ | R$^{10}$ | (R$^5$)$_n$ | R$^{10}$ | (R$^5$)$_n$ | R$^{10}$ | (R$^5$)$_n$ | R$^{10}$ | (R$^5$)$_n$ | R$^{10}$ | (R$^5$)$_n$ | R$^{10}$ | (R$^5$)$_n$ | R$^{10}$ |
| 3-Cl | H | 3-Br | H | 3-Cl | H | 3-Br | H | 3-Cl | H | 3-Br | H | 3-Cl | H | 3-Br | H |
| 3-Cl | Me | 3-Br | Me | 3-Cl | Me | 3-Br | Me | 3-Cl | Me | 3-Br | Me | 3-Cl | Me | 3-Br | Me |
| 3-Cl | Et | 3-Br | Et | 3-Cl | Et | 3-Br | Et | 3-Cl | Et | 3-Br | Et | 3-Cl | Et | 3-Br | Et |
| 3-Cl | n-Pr | 3-Br | n-Pr | 3-Cl | n-Pr | 3-Br | n-Pr | 3-Cl | n-Pr | 3-Br | n-Pr | 3-Cl | n-Pr | 3-Br | n-Pr |
| 3-Cl | i-Pr | 3-Br | i-Pr | 3-Cl | i-Pr | 3-Br | i-Pr | 3-Cl | i-Pr | 3-Br | i-Pr | 3-Cl | i-Pr | 3-Br | i-Pr |
| 3-Cl | n-Bu | 3-Br | n-Bu | 3-Cl | n-Bu | 3-Br | n-Bu | 3-Cl | n-Bu | 3-Br | n-Bu | 3-Cl | n-Bu | 3-Br | n-Bu |

TABLE 2-continued

| 3-Cl | i-Bu | 3-Br | i-Bu | 3-Cl | i-Bu | 3-Br | i-Bu | 3-Cl | i-Bu | 3-Br | i-Bu | 3-Cl | i-Bu | 3-Br | i-Bu |
| --- | --- | --- | --- | --- | --- | --- | --- | --- | --- | --- | --- | --- | --- | --- | --- |
| 3-Cl | s-Bu | 3-Br | s-Bu | 3-Cl | s-Bu | 3-Br | s-Bu | 3-Cl | s-Bu | 3-Br | s-Bu | 3-Cl | s-Bu | 3-Br | s-Bu |
| 3-Cl | t-Bu | 3-Br | t-Bu | 3-Cl | t-Bu | 3-Br | t-Bu | 3-Cl | t-Bu | 3-Br | t-Bu | 3-Cl | t-Bu | 3-Br | t-Bu |

| X is Br | | | | | | | | | | | | | | | |
| --- | --- | --- | --- | --- | --- | --- | --- | --- | --- | --- | --- | --- | --- | --- | --- |
| Z is N | | | | Z is CH | | | | Z is CCl | | | | Z is CBr | | | |
| $(R^5)_n$ | $R^{10}$ | $(R^5)_n$ | $R^{10}$ | $(R^5)_n$ | $R^{10}$ | $(R^5)_n$ | $R^{10}$ | $(R^5)_n$ | $R^{10}$ | $(R^5)_n$ | $R^{10}$ | $(R^5)_n$ | $R^{10}$ | $(R^5)_n$ | $R^{10}$ |
| 3-Cl | H | 3-Br | H | 3-Cl | H | 3-Br | H | 3-Cl | H | 3-Br | H | 3-Cl | H | 3-Br | H |
| 3-Cl | Me | 3-Br | Me | 3-Cl | Me | 3-Br | Me | 3-Cl | Me | 3-Br | Me | 3-Cl | Me | 3-Br | Me |
| 3-Cl | Et | 3-Br | Et | 3-Cl | Et | 3-Br | Et | 3-Cl | Et | 3-Br | Et | 3-Cl | Et | 3-Br | Et |
| 3-Cl | n-Pr | 3-Br | n-Pr | 3-Cl | n-Pr | 3-Br | n-Pr | 3-Cl | n-Pr | 3-Br | n-Pr | 3-Cl | n-Pr | 3-Br | n-Pr |
| 3-Cl | i-Pr | 3-Br | i-Pr | 3-Cl | i-Pr | 3-Br | i-Pr | 3-Cl | i-Pr | 3-Br | i-Pr | 3-Cl | i-Pr | 3-Br | i-Pr |
| 3-Cl | n-Bu | 3-Br | n-Bu | 3-Cl | n-Bu | 3-Br | n-Bu | 3-Cl | n-Bu | 3-Br | n-Bu | 3-Cl | n-Bu | 3-Br | n-Bu |
| 3-Cl | i-Bu | 3-Br | i-Bu | 3-Cl | i-Bu | 3-Br | i-Bu | 3-Cl | i-Bu | 3-Br | i-Bu | 3-Cl | i-Bu | 3-Br | i-Bu |
| 3-Cl | s-Bu | 3-Br | s-Bu | 3-Cl | s-Bu | 3-Br | s-Bu | 3-Cl | s-Bu | 3-Br | s-Bu | 3-Cl | s-Bu | 3-Br | s-Bu |
| 3-Cl | t-Bu | 3-Br | t-Bu | 3-Cl | t-Bu | 3-Br | t-Bu | 3-Cl | t-Bu | 3-Br | t-Bu | 3-Cl | t-Bu | 3-Br | t-Bu |

Utility

The selective oxidation of 2-pyrazolines with bromine of the present invention can be used to prepare a wide variety of compounds of Formula 1 that are useful as intermediates for the preparation of crop protection agents, pharmaceuticals and other fine chemicals. Among the compounds preparable according to the method of the present invention, compounds of Formulae 1a are particularly useful for preparing compounds of Formula 3

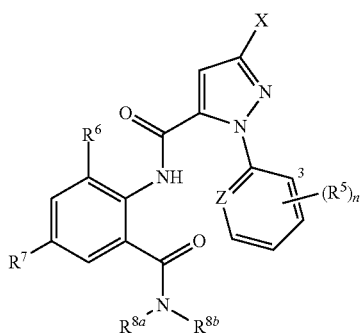

3 wherein X, Z, $R^5$ and n are defined as above; $R^6$ is $CH_3$, F, Cl or Br; $R^7$ is F, Cl, Br, I, CN or $CF_3$; $R^{8a}$ is $C_1$-$C_4$ alkyl and $R^{8b}$ is H or $CH_3$.

Compounds of Formula 3 are useful as insecticides, as described, for example, in PCT Publication No. WO 01/015518. The preparation of compounds of Formulae 2 and 3 are also described in WO 01/015518 and U.S. Patent Application 60/633,899, filed Dec. 7, 2004 [BA9343 US PRV] and hereby incorporated herein in their entirety by reference.

Compounds of Formula 3 can be prepared from corresponding compounds of Formula 1a by the processes outlined in Schemes 7-10.

Carboxylic acid compounds of Formula 1a wherein $R^{10}$ is H can be prepared by hydrolysis from corresponding ester compounds of Formula 1a wherein, for example, $R^{10}$ is $C_1$-$C_4$ alkyl. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp 224-269 for a review of methods). For compounds of Formula 1a, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 1a wherein $R^{10}$ is H. The carboxylic acid can be isolated by methods known to those skilled in the art, including extraction, distillation and crystallization.

As illustrated in Scheme 7, coupling of a pyrazolecarboxylic acid of Formula 1a wherein $R^{10}$ is H with an anthranilic acid of Formula 11 provides the benzoxazinone of Formula 12. In the method of Scheme 7, a benzoxazinone of Formula 12 is prepared directly via sequential addition of methanesulfonyl chloride to a pyrazolecarboxylic acid of Formula 1a wherein $R^{10}$ is H in the presence of a tertiary amine such as triethylamine or pyridine, followed by the addition of an anthranilic acid of Formula 11, followed by a second addition of tertiary amine and methanesulfonyl chloride. This procedure generally affords good yields of the benzoxazinone of Formula 12.

Scheme 7

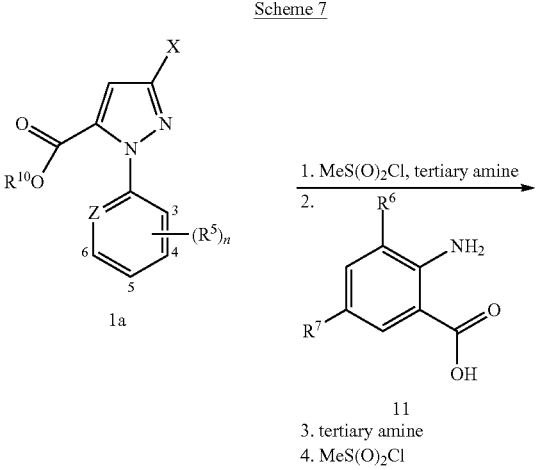

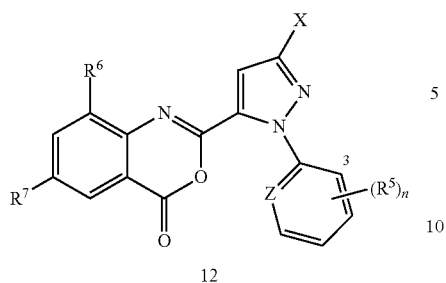

12 wherein $R^5$, $R^6$, $R^7$, X, Z and n are as defined for Formula 3.

An alternate method for the preparation of benzoxazinones of Formula 12 is shown Scheme 8, involving coupling of a pyrazole acid chloride of Formula 14 with an isatoic anhydride of Formula 13 to provide the Formula 12 benzoxazinone directly.

Scheme 8

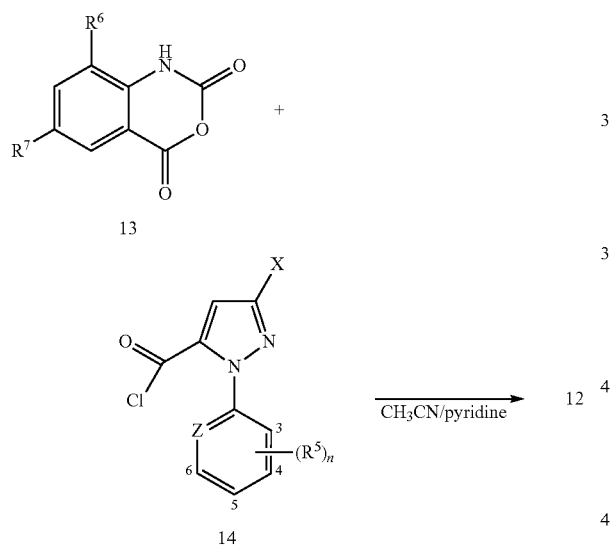

wherein $R^5$, $R^6$, $R^7$, X, Z and n are as defined for Formula 3.

Solvents such as pyridine or pyridine/acetonitrile are suitable for this reaction. The acid chlorides of Formula 14 are available from the corresponding acids of Formula 1a wherein $R^{10}$ is H by known procedures such as chlorination with thionyl chloride or oxalyl chloride.

Compounds of Formula 3 can be prepared by the reaction of benzoxazinones of Formula 12 with amines of $NHR^{8a}R^{8b}$ of Formula 15 as outlined in Scheme 9.

Scheme 9

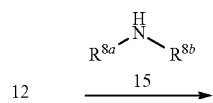

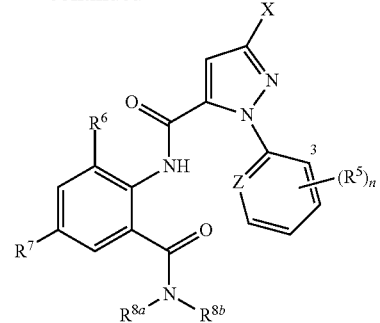

3 wherein $R^5$, $R^6$, $R^7$, $R^{9a}$, $R^{8b}$, X, Z and n are as previously defined for Formula 3. The reaction can be run neat or in a variety of suitable solvents including acetonitrile, tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Bioorganic and Medicinal Chemistry* 2000, 8, 2095-2103 and references cited within. See also Coppola, *J. Heterocyclic Chemistry* 1999, 36, 563-588.

Compounds of Formula 3 can also be prepared by the method shown in Scheme 10. The direct coupling of compounds of Formula 11 with compounds of Formula 1a wherein $R^{10}$ is H, using a suitable coupling reagent such as methanesulfonyl chloride provides the anthranilamides of Formula 3.

Scheme 10

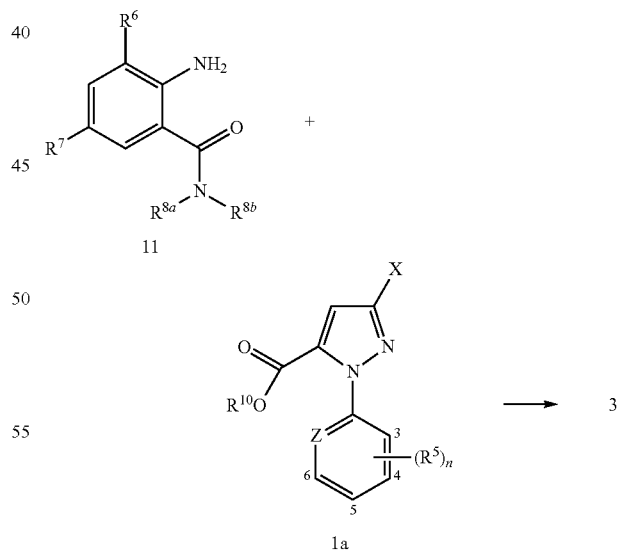

Whatever the means for converting a compound of Formula 1a to a compound of Formula 3, this invention provides an effective method of preparing the compound of Formula 3 that is characterized by preparing the compound of Formula 1a by the method of preparing a compound of Formula 1 as described above.

What is claimed is:

1. A method for preparing a compound of Formula 1a

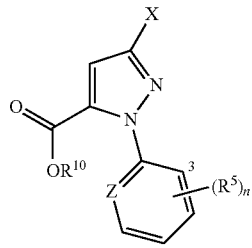

wherein
X is halogen, $OR^3$ or $C_1$-$C_4$ haloalkyl;
Z is N or $CR^9$;
$R^9$ is H, halogen or $C_1$-$C_4$ haloalkyl;
$R^{10}$ is H or $C_1$-$C_4$ alkyl;
$R^3$ is H or $C_1$-$C_4$ haloalkyl;
each $R^5$ is independently halogen or $C_1$-$C_4$ haloalkyl; and
n is an integer from 0 to 3;
comprising:
contacting a 2-pyrazoline of Formula 2a

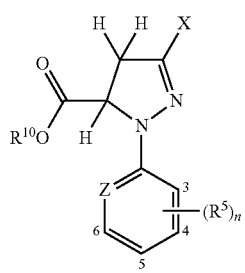

with bromine at a temperature of 120-140° C.

2. The method of claim 1 wherein
X is Br or $CF_3$;
Z is N;
each $R^5$ is independently halogen or $CF_3$; and
$R^{10}$ is methyl or ethyl.

3. The method of claim 1 wherein
X is OH, $OCF_2H$ or $OCH_2CF_3$;
Z is N;
each $R^5$ is independently halogen or $CF_3$; and
$R^{10}$ is methyl or ethyl.

4. The method of claim 1 further comprising combining a base with the compound of Formula 2a either before or after contacting with the bromine and the molar equivalent of base relative to bromine is about 0:1 to 4:1.

5. The method of claim 1 wherein the bromine is present relative to the compound of Formula 2a at a molar equivalent of about 2:1 to 1:1.

6. The method of claim 1 further comprising combining a solvent with the compound of Formula 2a to form a mixture, before contacting the compound of Formula 2a with the bromine and the temperature is about the boiling point of the solvent.

7. The method of claim 1 further comprising adding the bromine as a gas to the compound of Formula 2a and the gaseous bromine is diluted with an inert gas.

8. The method of claim 6 wherein the solvent is an optionally halogenated hydrocarbon with a boiling point higher than 100° C.

9. The method of claim 8 wherein the solvent is an optionally chlorinated aromatic hydrocarbon or dibromoalkane.

10. The method of claim 8 wherein the optionally halogenated hydrocarbon is t-butylbenzene, chlorobenzene or 1,2-dibromoethane.

11. The method of claim 9 wherein the optionally halogenated hydrocarbon is chlorobenzene.

12. The method of claim 1 further comprising adding the bromine as a liquid to the compound of Formula 2a.

13. A method for preparing a compound of Formula 1a

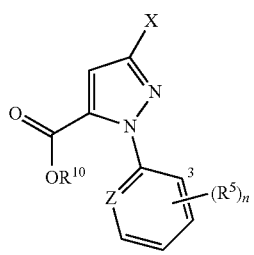

wherein
X is halogen, $OR^3$ or $C_1$-$C_4$ haloalkyl;
Z is N or $CR^9$;
$R^9$ is H, halogen or $C_1$-$C_4$ haloalkyl;
$R^{10}$ is H or $C_1$-$C_4$ alkyl;
$R^3$ is H or $C_1$-$C_4$ haloalkyl;
each $R^5$ is independently halogen or $C_1$-$C_4$ haloalkyl; and
n is an integer from 0 to 3;
comprising:
contacting a 2-pyrazoline of Formula 2a

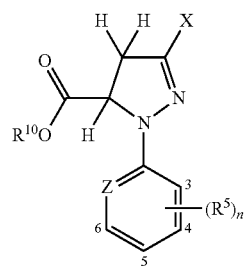

in an optionally halogenated hydrocarbon solvent with a boiling point higher than 100° C. to form a mixture before contacting the 2-pyrazoline of Formula 2a with bromine.

* * * * *